United States Patent [19]

Rubin

[11] Patent Number: 5,240,914
[45] Date of Patent: Aug. 31, 1993

[54] METHOD AND COMPOSITIONS FOR INHIBITING TUMOR CELL METABOLISM

[75] Inventor: David Rubin, 8949 Montrose Way, San Diego, Calif. 92122

[73] Assignees: Adolph Schwimmer, New York, N.Y.; David Rubin, San Diego, Calif.

[21] Appl. No.: 995,013

[22] Filed: Dec. 22, 1992

Related U.S. Application Data

[63] Continuation-in-part of Ser. No. 830,150, Feb. 3, 1992, abandoned.

[51] Int. Cl.$^5$ ............................................. A61K 31/70
[52] U.S. Cl. ................................... 514/23; 536/1.11; 536/4.1; 424/717
[58] Field of Search ................... 514/23; 536/1.1, 4.1; 424/717

[56] References Cited

U.S. PATENT DOCUMENTS

| | | | |
|---|---|---|---|
| 4,327,074 | 4/1982 | Rubin et al. | 424/9 |
| 4,337,760 | 7/1982 | Rubin | 536/17.9 |
| 4,424,348 | 1/1984 | Rubin | 536/4.1 |
| 4,426,372 | 1/1984 | Burch | 424/10 |
| 4,481,195 | 11/1984 | Rubin | 536/4.1 |
| 4,584,368 | 4/1986 | Rubin | 536/4.1 |
| 4,645,661 | 2/1987 | Schonbaum | 514/476 |
| 4,762,705 | 8/1988 | Rubin | 530/351 |
| 4,895,874 | 1/1990 | Rubin et al. | 514/558 |
| 4,938,949 | 7/1990 | Borch et al. | 514/476 |
| 5,002,755 | 3/1991 | Mitchell et al. | 424/10 |
| 5,005,588 | 4/1991 | Rubin | 514/557 |
| 5,035,878 | 7/1991 | Borch et al. | 514/483 |

*Primary Examiner*—Ronald W. Griffin
*Attorney, Agent, or Firm*—Browdy and Neimark

[57] ABSTRACT

The metabolism of tumor cells which have $\beta$-glucuronidase activity is inhibited by administering to a patient a conjugate of glucuronic acid and a thiocarbamate compound of the formula:

$$R^1R^2C\overset{S}{\underset{\|}{S}}-M^+$$

wherein $R^1$ and $R^2$ are selected from the group consisting of $C_1-C_6$ alkyl and $C_1-C_6$ cycloaliphatic, and M is selected from the group consisting of hydrogen, an electropositive, ionically bonded metal, and the radical $$-S\overset{S}{\underset{\|}{C}}NR^3R^4$$

and $R^3$ and $R^4$ are selected from the group consisting of $C_1-C_6$ alkyl and $C_1-C_6$ cycloaliphatic groups.

18 Claims, No Drawings

METHOD AND COMPOSITIONS FOR INHIBITING TUMOR CELL METABOLISM

This application is a continuation-in-part of Ser. No. 07/830,150, filed Feb. 3, 1992, now abandoned, the entire contents of which are incorporated herein.

FIELD OF THE INVENTION

The present invention is directed to a method and composition for treating tumors exhibiting β-glucuronidase activity, and, more specifically, to a method and composition for treating tumors exhibiting β-glucuronidase activity by preventing metabolism of tumor cells.

BACKGROUND OF THE INVENTION

Control of cell growth is one of the most important aspect of an animal's physiology. The cells of an adult must divide frequently enough to allow tissues to remain in a steady state, and division must be stimulated at wounds or when special requirements are placed on a tissue. There must be many circulating cell-specific factors that signal individual cell types whether to divide or not. However, uninhibited cell growth results in tumors.

Malignant tumors can be differentiated from benign tumors by two major characteristics: invasiveness and spread. Malignant tumors do not remain localized and encapsulated, as do benign tumors. The malignant tumors invade surrounding tissues, invade the body's circulatory system, and set up areas of proliferation away from the site of their original appearance. Cancer cells have abnormal and unstable numbers of chromosomes, as well as many chromosomal abnormalities.

One of the major limitations of effective cancer chemotherapy is toxicity to normal tissues. Agents that are effective killers of neoplastic cells are usually also detrimental to normal cells, particularly to rapidly proliferative cells of the gastrointestinal tract and bone marrow. Some attempts have been made to deliver chemotherapeutics more directly to cancer cells by the use of antibody-drug conjugates, as described by Hurwitz in *Optimization of Drug Delivery*, Alfred Benzon Symposium 17, Editors, Hans Bundgaard et al., Munksgaard, Copenhagen, 1982. However, in this case, antibodies specific to the tumor must be used in order to provide the specificity of delivery required for this technique to be useful. More importantly, however, there has been no demonstration that this approach would be feasible in solid tumor systems, particularly in those which have a tendency to metastasize.

Nickel and certain of its diverse compounds are well known to be carcinogenic, and nickel carbonyl is the most carcinogenic of the inhaled nickel compounds. Inhalation of nickel carbonyl will produce lung cancer within a period of two years in Wistar rats, a species unusually resistant to lung cancer, and nickel subsulfide appears to have the greatest carcinogenic potential of the inorganic nickel compounds when injected into striated muscle or testes of experimental animals. Various soluble salts of diethyldithiocarbamate have been found to exert a detoxifying effect against the acute inhalation of lethal quantities of nickel carbonyl by warm-blooded animals, Sunderman et al., *Annals of Clinical and Laboratory Science* 14 (1):1-9, 1984. The soluble salts of diethyldithiocarbamate were found to inhibit carcinogenesis in rats chronically subjected to nickel subsulfide by muscular implantations (Sunderman et al., op. cit.). The diethyldithiocarbamates were found to bind nickel successfully, and met the criteria of a clinically useful metallic chelating agent: (1) non toxic; (2) relatively specific for the metal to be mobilized; and (3) capable of forming a stable excretable complex of the metal.

Sodium diethyldithiocarbamate has also been used as a potentiating agent for levamisole in treating cancer, Renoux, *TIPS* 248-249, 1981. Sodium diethyldithiocarbamate has been found, in high doses such as above 200 mg/kg, to potentiate barbital sleep, inhibit dopamine beta-hydroxylase and depress brain norepeniphrine levels. At doses of up to 600 mg/kg levels, sodium diethyldithiocarbamate induces retrograde amnesia of trained passive avoidance and cerebral seizure in the rat. This compound also prevents the development of chemically-induced diabetes. As a chelating agent, sodium diethyldithiocarbamate is used in the treatment of metal poisoning without toxic or untoward side effects at daily doses of 30-50 mg/kg body weight.

There has been no evidence of carcinogenicity of the diethyldithiocarbamate when administered in the feed for 104-109 weeks to rats and mice. The incidence of spontaneous tumors was lower in the dosed groups than in the corresponding control group. Additionally, the diethyldithiocarbamate was found to exert a protective effect against a variety of chemically-induced malignant tumors, and against ionizing radiation.

When used in immunostimulant doses of about 0.5-25 mg/kg, diethyldithiocarbamate evidences a unique influence on the immune system in inducing the recruitment of T cells for undifferentiated precursor cells. This influence is mediated through the increased synthesis of hormone-like factors active on the T-cell lineage. The diethyldithiocarbamate induces T cells to generate enhanced levels of cytotoxic activity and responses to alloantigens, macrophages and monocytes to participate in delayed-type hypersensitivity, resting T cells to develop suppressive activities, and B cells to secrete antibodies of the IgG class. These activities are probably associated with an increase in the number of Lyt−1+ T cells which provide the signal for help to increase the response of other cell subsets when needed. Diethyldithiocarbamate is devoid of direct influence on B cells, nonspecific polyclonal activity, and in vitro augmenting effects, and has no sensitizing or pyrogenic influence.

Perchellet et al. reported in *Cancer Research* 47: 6302-6309, 1987, that diethyldithiocarbamate injected intraperitoneally inhibits 12-O-tetradecanoylphorbol-13-acetate(TPA)-decreased glutathione peroxidase and TPA-induced ornithine decarboxylase activities in mouse epidermis in vivo. Diethyldithiocarbamate is more potent in inhibiting these effects of TPA than sixteen other antioxidants, free radical scavengers, thiol-containing compounds, and reduced glutathione level-raising agents, even though some of these treatments are applied directly to the TPA-treated skin. The powerful and long-lasting inhibitory effects of diethyldithiocarbamate affect both the first and second stages of skin tumor promotion.

However, because the diethyldithiocarbamate is injected intraperitoneally, it is likely that only very small fractions of the doses of diethyldithiocarbamate actually reach the target cells. Because there is a good correlation between polyamine and DNA synthesis, there is little doubt that the sequential induction of ornithine decarboxylase activity and macromolecule synthesis by TPA may be essential for the epithelial hyperproliferation associated with the later stages of skin tumor promotion. Moreover, the induction of epidermal DNA synthesis, but not ornithine decarboxylase activity, may be necessary for the conversion phase of skin carcinogenesis elicited when TPA is used as a stage 1 promoter. Since undisturbed DNA synthesis may be an essential component of several stages of tumor promotion, the efficacy of diethyldithiocarbamate against both the first and second stages of skin tumor promotion may be linked to its ability to inhibit DNA synthesis in conjunction with its antioxidant property.

There have been many reports in the prior art relating to the general concept of providing direct transport of an agent which is toxic to tumor cells directly to tumors having β glucuronidase activity by conjugating the agent with glucuronic acid. Among such reports are Von Ardenne, M. et al., *Agressologie*, 1976, 176(5):261-264; East German Patent No. 122,386; German Offenlegungsschrift 22 12 014; Sweeney et al., *Cancer Research* 31:477-478, 1971; Baba et al., *Gann.* 69:283-284; and Ball, *Biochem. Pharm* 23:3171-3177 (1974).

Von Ardenne suggest broadly many types of aglycones which may be conjugated to glucuronic acid and will be active at the tumor site. There include, broadly, alkylating groups, antimetabolites, cytotoxins, membrane-active (lytic) groups, glycolysis stimulators, respiration inhibitors, inorganic and organic acids and cell cycle stoppers. The East German patent also suggests many such combinations, including 5-fluorouracil-glucuronide, aniline mustard-glucuronide and many others. The Offenlegungsschrift also mentions a large number of glucuronides. Sweeney et al. disclose the anti-tumor activity of mycophenolic acid-β-D-glucuronides. Baba et al. note the anti-tumor activity of 5-fluorouracil-o-β-D-glucuronide, and Ball discloses the anti-tumor activity of p-hydroxyaniline mustard glucuronide.

Rubin, in U.S. Pat. Nos. 4,337,760 and 4,481,195, discloses methods for treating tumors having high β-glucuronidase activity with glucuronides with aglycones toxic to the tumor cells with great safety toward the rest of the body by first administering an alkalinizing agent in an amount sufficient to maintain the pH level of non-tumor tissues at approximately 7.4 during the glucuronide treatment to inactivate β-glucuronidase activity in the rest of the body. Thus, the toxic agent is directed only to the cancer cells, as opposed to all of the healthy cells of the body, since the aglycone is only released at the cancer site. Tumors having high glucuronidase activity can be identified by assaying tumor cells obtained in a biopsy for β-glucuronidase activity, or by administering a glucuronide whose aglycone has been labelled with a radioactive isotope. If upon a full body scan it is found that the radioisotope is accumulated at any specific areas of the body, this will indicate not only the location of the tumor but the fact that the tumor has sufficient β-glucuronidase activity to deconjugate the glucuronide.

Borch, in U.S. Pat. No. 4,426,372, discloses that the toxicity of platinum (II) compounds used for treating tumors can be countered by administering dithiocarbamic compounds parenterally in a timely fashion. The cellular DNA is first exposed to platinum (II), and then the dithiocarbamic compound is administered. The dithiocarbamic compound is administered within six hours of platinum administration. The mode of administration of the dithiocarbamate is important, because acidic aqueous media, conjugating sugars, uronates, glycosides, liver tissue and other media or agents encountered in living biological systems can inactivate dithiocarbamic toxicity inhibitors long before the inhibitors can bind to the platinum. In addition, it has been found that alkali metal dithiocarbamates are sufficiently powerful platinum-binding compounds to dislodge the platinum from DNA/Pt(II) complexes formed in vitro.

The dithiocarbamates are also well known chelating agents for other metals such as zinc and copper.

SUMMARY OF THE INVENTION

It is an object of the present invention to overcome the aforementioned deficiencies of the prior art.

It is an object of the present invention to provide a method and composition for treating tumor cells.

It is another object of the present invention to provide a composition and method for treating tumor cells without damaging normal cells.

According to the present invention, glucuronide conjugates of thiol metal chelating agents are delivered directly to a tumor site where the β-glucuronidase present in the tumor cells cleaves the conjugate, releasing the metal chelating agent directly at the site of the tumor cell. The metal chelating compound then chelates zinc, copper or other transition metals present in the DNA locus of the cells, thus preventing cell metabolism. Without the ability to metabolize, the tumor cells die. Since undisturbed DNA synthesis may be an essential component of several stages of tumor promotion, the efficacy of the chelating agents against tumor promotion may be linked to the ability of these chelating agents to inhibit DNA synthesis.

In order to treat tumor cells successfully with the thiol chelating agents of the present invention it is essential to protect the thiol chelating agents used in the present invention from the action of bodily fluids and tissues until the chelating agent reaches the tumor site, because acidic aqueous media, conjugating sugars, uronates, glycosides, liver tissue and other media or agents encountered in living biological systems can inactivate the chelating ability of these thiol compounds, and thus their toxicity to dividing cancer cells. The thiol compounds that can be used to chelate the necessary metals at the tumor site and thus inactivate tumor cell division have the structure

wherein $R^1$ and $R^2$ are the same or different and represent electron-donating lower aliphatic or lower cycloaliphatic radicals, i.e., radicals having fewer than 6 carbon atoms; and M is selected from the group consisting of hydrogen, an electropositive, ionically bonded metal, and the radical

wherein $R^3$ and $R^4$ are defined in the same manner as $R^1$ and $R^2$.

Dithiocarbamic compounds have an extraordinarily powerful capability for complexing with transition metals. The functional group that is believed to be formed in square planar complexes is

—N—CS—S— which is believed to be one of the most stable complexes formed. This functional group has a chelating or ligand-forming effect which is almost impossible to reverse with other chelating agents. Consequently, dithiocarbamic compounds have the ability to substitute for or displace or reverse most other transition metal complexes or chelates.

Ammonias and amines, for example, are moderately strong ligands in transition metal coordination complexes, but dithiocarbamates can displace them, liberating the free ammonia or amines. Although the present invention is not bound by any theory, it is believed that both the thiocarbonyl and the thiol sulfurs of the dithiocarbamic functional group can form strong coordinate bonds with transition metals. The function of the amido nitrogen in the dithiocarbamic structure is believed to be generally activating in nature, perhaps due to the unbonded electron pair on the nitrogen. Accordingly, it should follow that electron-donating groups substituted on the amido nitrogen should further intensify the activity of the two sulfur atoms. It would also be expected that electron-withdrawing groups substituted on the nitrogen would decrease the activity of the sulfurs.

Saturated and non-conjugated unsaturated aliphatic and cycloaliphatic groups are known to have a mild electron-donating effect and are particularly suitable for substitution on the amido nitrogen of the dithiocarbamic structure. "Lower" aliphatic or cycloaliphatic radicals, in the context of the present invention, are generally considered to be those containing from one to six carbon atoms. These radicals, particularly radicals having from one to three carbon atoms, do not detract significantly from the solubility of monomeric dithiocarbamic compounds in polar solvents. In addition, these groups do not introduce any acute toxicity aspect to the dithiocarbamic compound.

In the case where both $R^1$ and $R^2$ are ethyl, i.e., diethyldithiocarbamic acid, the resulting structure has particularly low toxicity and is particularly suitable for administration to living organisms. For maximum solubility in polar solvents, the preferred compounds have the structure $$R^1R^2NC\overset{S}{\underset{\|}{\phantom{N}}}SM$$

wherein $R^1$ and $R^2$ are as defined previously, and M is an electropositive, ionically bonded metal, which is pharmaceutically acceptable.

Structures of this type, when cleaved from the glucuronide conjugate, can dissociate into the corresponding dithiocarbamate ion and an $M^+$ cation in aqueous media, and thus are particularly useful for delivery to a tumor site. Accordingly, pharmaceutically acceptable cations such as the alkali metal cations, particularly sodium and potassium, are preferred.

Dithiocarbamates and related compounds have been reviewed extensively with respect to their chelating ability in a work by G. D. Thorn et al. entitled "The Dithiocarbamates and Related Compounds," Elsevier, New York, 1962. In addition, diethyldithiocarbamate has been successfully used in analytical techniques for measuring Pt(II) in urine, Borch et al., *Analytical Letters* B12:917 (1979). It is also known that diethyldithiocarbamate salts can reverse the coordination in various coordinate complexes of transition metals, cf. Sundermann in *Ann. Clin. Res.* 3:182 (1971).

Glucuronides of diethyldithiocarbamic acid are known to be formed biosynthetically in broken- and intact-cell preparations of mouse liver, Dutton et al., *Biochem. J.* 129, 539–550, 1972. Additionally, Gessner et al., in *Biochemical Pharmacology* 21:219–230, 1972, disclose that the glucuronide conjugate of diethyldithiocarbamate is the major urinary metabolite of diethyldithiocarbamate accounting for about 30% of the metabolic products captured in the urine. However, these substances have never been synthesized or otherwise prepared in pure form.

The thioglucuronides can be synthesized by the following reaction:

R-SH +

UDP-glucuronic acid $\xrightarrow{\text{UDP-glucuronyltransferase}}$

R-S-glucuronide + UDP.

Alternatively, the conjugates can be prepared by the methods disclosed in Rubin, U.S. Pat. No. 4,481,195 and Rubin, U.S. Pat. No. 4,424,348, the entire contents of both of which are incorporated by reference.

For example, the thiols are conjugated to glucuronic acid by conjugation of the thiol with methyl(tri-O-acetyl-α-D-glucopyranosyl bromide)-uronate, which is the active form of glucuronic acid, and may be produced in accordance with the teachings of Bollenback, et al., *J. Am. Chem. Soc.* 77:3310, 1955.

The thiol is introduced to the methyl(tri-O-acetyl-α-D-glucopyranosyl)bromide uronate in a solution of the thiol catalyzed by a small catalytic amount of silver oxide. There may also be used, as solvent, quinoline, methyl nitrile or methyl cyanide. Silver carbonate may also be used as the catalyst. This method yields the tri-acetyl conjugate, which has been found to be particularly useful because the acetyl groups are not easily removed, so that the triacetylated compounds are even less toxic to normal cells than the free acid form of the conjugates.

Another method of condensation is to use sodium or potassium hydroxide as the condensing agent in aqueous acetone solution. A stoichiometric excess of the thiol is preferably used. The reaction solution is maintained at room temperature for 24 hours or until the reaction is complete:

The acid is produced by reaction of the triacetyl methyl ester obtained above with a ½ molar amount of 0.5N barium hydroxide which is added slowly to this solution to form a white precipitate. Preferably, an excess of barium hydroxide is added until there is no more precipitation.

The addition of 0.5N sulfuric acid, volume to volume, followed by cooling in ice water for 20 minutes, releases the free glucuronides.

The mixture is then filtered, and the supernatant is dried in vacuum and crystallized from ether.

These conjugates are readily hydrolyzed by β-glucuronidase to release the thiol chelating compound at the site of the β-glucuronidase active tumor by the action of the enzyme on the conjugate.

The triacetylated form of the glucuronide is the preferred form of the compounds to be used in accordance with the present invention. However, in addition to the free acid form of the conjugate, other pharmaceutically acceptable esters may be used, although in most cases it would be expected that their activity would be somewhat less due to their relatively lower affinity to β-glucuronidase. Therefore, whenever the term "glucuronide compound" is used in the present specification and claims, it is understood to include not only the free glucuronic acid form of the conjugate but also pharmaceutically acceptable salts and esters thereof as discussed hereinabove.

The triacetylated form of the conjugate is the preferred form to use, as the acetylation provides an additional safety factor for normal cells in the body. These acetyl groups are not easily removed, so that the triacetylated conjugates are not particularly cytotoxic to normal cells. However, since primitive cells, such as growing cancer cells, can produce many different types of enzymes, including acetylase, these primitive cells can readily remove the acetyl groups on the acetylated conjugates to provide active forms of the compound directly at the site of a growing tumor. The tri-acetylated conjugates are lipid soluble and are retained by the body at the tumor site for a much longer period of time than the free acid form of the conjugates. The tri-acetylated conjugates have also been found able to cross the blood-brain barrier, so that they can be used for treating tumors having β-glucuronidase activity in the brain.

The reason that the tri-acetylated conjugates are particularly useful for treating tumor cells is because primitive cells can produce acetylase along with a great variety of other enzymes, and this acetylase removes the acetyl groups from the conjugate. The more anaplastic (more immature) the tumor cells, the more enzymes they produce, so that the triacetylated form of the conjugated drug is more selectively toxic to tumor cells than even the conjugated acid form. Thus, since two steps are required to liberate the cytotoxic compound, the acetylated conjugates are even more preferentially delivered to the site of an active tumor than are the acid form of the conjugates.

The selectivity of glucuronide compounds toward tumors can be greatly increased and the possible deconjugation of the toxic aglycones in healthy parts of the body can be greatly minimized by administering to the patient, prior to or simultaneously with administration of the glucuronide, an alkalinizing agent which will maintain the pH of the rest of the body at a pH of about 7.4. It is known that the activity of β-glucuronidase activity is substantially nil at a pH of about 7.4. Thus, the administration of alkalinizing agents such as bicarbonates or other basic salts will substantially decrease and eliminate β-glucuronidase activity which occurs naturally in certain healthy tissues such as the kidneys, spleen and liver. Such an administration of alkalinizing agent will not diminish the acidity of the tumor cells themselves, however, in view of the naturally low pH of the tumor cells, the mechanism of prior hyperacidification and the lack of substantial blood perfusion through the tumor area, as well as other possible mechanisms. It has been suggested in the literature, in fact, that bicarbonate will actually increase the acidity of the cancer cells, cf. Gullino et al., *J.N.C.I.* 34 (6):857–869, 1965.

Since the β-glucuronidase activity of the tumor cells is enhanced by acidification, and the β-glucuronidase activity of the rest of the body, particularly of the kidneys, will be substantially eliminated by alkalinization, the cytotoxic thiols will only be released at the tumor site itself due to deconjugation of the glucuronides by the action of β-glucuronidase. Without the alkalinization step, substantial amounts of toxic materials may be released, for example in the kidneys, and the cytotoxic thiols so released may cause substantial damage to these organs. Thus, only through the use of the present invention can glucuronides of thiol chelating compounds which are toxic to tumor cells be used with great degree of safety and efficacy. The greater the toxicity of the thiol chelating compounds, the more important is the alkalinization step. Use of the triacetylated form of the conjugates provides an additional degree of safety for normal cells, as only the tumor cells produce sufficient acetylase to liberate the free acid conjugate.

Other steps for increasing β-glucuronidase activity at the tumor cells may also be undertaken. One method of accomplishing this is to elevate the temperature of the toxic cells at the time of treatment. This may be done by elevating the temperature of the entire body such as by use of a pyrogenic drug or by elevating the temperatures solely in the area of the toxic cells, such as by microwave radiation or electrical current. Raising of the temperature increases β-glucuronidase activity, thereby increasing the efficiency of the deconjugation of the glucuronides. It is known that an elevation of body temperature of 3° C. increases β-glucurodinase activity by 50%.

Known pyrogenic drugs include etiocholanolone, progesterone, dinitrophenol, dinitrocresol, and the like. Because dinitrophenol and dinitrocresol are also cytotoxic, the use of these compounds are preferred, particularly when they are administered as the glucuronide.

Local hyperthermia in the region of suspected tumor cells is preferred to general hyperthermia, because general hyperthermia will also increase the β-glucuronidase activity in healthy cells. However, because of the alkalinization step, this is not a major problem. If the hyperthermia is local, then this provides an additional degree of certainty that the glucuronides will only become deconjugated at the tumor site. The application of microwave treatment directed at the suspected tumor site is one way to achieve total hyperthermia. Due to the different electrical resistance of tumor cells, another method of achieving some degree of local hyperthermia is by administering a low electrical current through the body.

A further manner of increasing β-glucuronidase activity selectively at tumor cells is by administration of estrogen to female patients or testosterone to male patients, for tumors which are not estrogen- or testosterone-dependent. It has been reported that these compounds induce β-glucuronidase activity in trophoblastic cells. Since certain tumor cells are known to be trophoblastic, this method is particularly useful for those types of cells. The alkalinization step would prevent damage to healthy trophoblastic cells.

Before treatment of patients in accordance with the present invention, it should be ascertained that the particular type of tumor involved has a high β-glucuronidase activity. This may be done in a number of ways. One way is to assay tumor cells obtained in a biopsy for β-glucuronidase activity. If such a test is positive, then the pharmaceutical compositions of the present invention may be administered.

A second method is the administration of a glucuronide whose aglycone has been labelled with a radioactive isotope. If, upon a full body scan, it is found that the radioisotope is accumulated at any specific areas of the body, then this will indicate not only the location of the tumor but the fact that the tumor has sufficient β-glucuronidase activity to deconjugate the glucuronide. If there are no tumors present, or if the tumors are of the type which do not have β-glucuronidase activity, then there will be no accumulation of radioisotope in the body as the alkalinization step of the present invention eliminates all β-glucuronidase activity and the isotope will be passed through the body.

Another method of diagnosing tumors which are treatable by means of the present invention is to test for the presence of free glucuronic acid in the urine. While the presence of glucuronides in the urine is common, the presence of free glucuronic acid in the urine, and particularly the presence of increasing amounts of glucuronic acid when tested over a period of several days, is a potent indication of the presence of tumors with β-glucuronidase activity. It is hypothesized that the presence of free glucuronic acid in the urine in cancer patients is caused by the action of β-glucuronidase in the cancer cells on the intercellular filaments and connective tissue. Glucuronic acid is a reaction product of such activity because the intercellular filaments and connective tissues ar composed of polymers of which glucuronic acid is an element and which are known substrates for the enzyme β-glucuronidase.

Free glucuronic acid can readily be distinguished from conjugated glucuronides in theurine. Both glucuronides and glucuronic acid give a chromogenic complex with tetraborate in concentrated sulfuric acid, which complex reacts with m-hydroxydiphenyl to create a colored water-soluble complex. When lead acetate is added at an alkaline pH, the glucuronides precipitate and the addition of dithizone (dithiosemicarbazone) makes a stable complex with the excess lead. Accordingly, an optical reading may be taken representative of the amounts of total glucuronides and free glucuronic acid after tetraborate and m-hydroxydiphenyl have been added. A second reading may then be taken after the conjugated glucuronides and excess lead have been removed from the aqueous phase by the addition of basic lead acetate and after ditizone has been added. Alternatively, the conjugated glucuronides can be removed by reaction with barium hydroxide. The addition of barium hydroxide to the urine sample will cause precipitation of the conjugated glucuronides but not of the free glucuronic acid. After centrifugation and filtration the conjugated glucuronides are eliminated and what remains is only the free glucuronic acid. A reading representative of the amount of free glucuronic acid many then be taken. The alternative procedure bypasses the necessity of the use of dithizone.

In the urine test for glucuronidase activity, normal patients exhibit between 200 and 400 mg per 24 hours of free glucuronic acid in the urine. Cancer patients with well developed tumors which have β-glucuronidase activity show greater than 200 to 7000 mg per 24 hours free glucuronic acid. Accordingly, using this above test, if more than about 400 mg per 24 hours of free glucuronide is exhibited, this is an excellent indication of the presence of tumors having a high β-glucuronidase activity.

A negative indication on this urine test will not conclusively rule out the presence of tumors having β-glucuronidase activity, because tumors in their initial stages, although they might have β-glucuronidase activity, might not release sufficient free glucuronic acid to cause a positive reading of the urine. Therefore, the urine test should be repeated, and if an increasing amount of free glucuronic acid is found, then this is another indication of the presence of a tumor having β-glucuronidase activity.

Once it has been determined that the patient has a tumor having β-glucuronidase activity, the first step of the treatment is to administer a dose of glucose as, for example 100 g of honey, glucose, or other simple sugar. Approximately one hour later, an intravenous drip is begun of a solution in distilled water containing approximately 10% glucose and 60 milliequivalents sodium bicarbonate. Approximately 1 liter is administered, assuming no contraindications, and the pH of the urine is checked to determine that it has reached a pH of approximately 7.4. This will establish that the system has become alkalinized and it is no safe to administer the glucuronide. Another liter of the same glucose-bicarbonate solution, but also including the desired amount of glucuronide, is then administered. This is repeated daily as needed.

If there are contraindications for the administration of bicarbonate, then an antacid may be orally administered. This antacid may be any conventional antacid such as sodium bicarbonate, magnesium bicarbonate, aluminum hydroxide, aluminum magnesium silicate, magnesium carbonate, magnesium hydroxide, magnesium oxide, or the like. The important criterion is that the pH of the urine become approximately 7.4 and remain so during treatment.

The hyperacidification of the tumor cells is caused by a hyperglycemic condition in the patient. Therefore, any hyperglycemic agent may be used as the hyperacidification agent, as, for example, fructose, galactose, lactose or glucagon. Furthermore, it should be understood that this hyperglycemic condition may be effected in any known manner. For example, if the patient is diabetic, then the condition can be brought about by decreasing the insulin administration.

Any agent which will raise the pH of the urine to approximately 7.4 can be used as the alkalinizing agent, including sodium or potassium bicarbonate or citrate, or other basic salts or antacids. While it is preferred that these agents be administered intravenously, they may be administered orally.

When the term "approximately 7.4" is used in the present specification and claims, with respect to the pH level to be maintained in the rest of the body, it should be understood that a pH level slightly above or below 7.4 may be used, although this is not preferred. As the pH deceases from 7.4, the β-glucuronidase activity increases until the optimal pH is reached. Furthermore, below pH 7.0 the rest of the body will not be alkaline but will be acid. Above 7.4 the danger of alkalosis increases without any substantial further decrease in β-glucuronidase activity. A pH level of 7.4 is preferred, as this is physiological pH and cannot be harmful to the body, and it is known that the β-glucuronidase activity in healthy organs is substantially nil at this pH level.

The dosage of the compounds administered should be monitored to avoid any side effects due to the massive release of toxins caused by the dying cancer cells. It may be preferable to treat the patient with the conjugates of the present invention in short courses of several days, leaving several days in between to allow any toxins released by the dying cancer cells to leave the body before continuing with treatment.

Besides intravenous administration, the glucuronide conjugates of the present invention may be administered by any means of parenteral administration. However, the glucuronides in the free acid form should not be administered orally, as it is known that $\beta$-glucuronidase is present in the digestive tract, and therefore would destroy the conjugates and release the toxic thiol before it reached the site of the cancer. However, the acetylated form of the conjugates can be administered orally, since this form requires acetylase to liberate the free acid form and there is insufficient acetylase in the normal gastrointestinal tract to liberate the free acid form of the conjugate.

The amount of glucuronide conjugate to be administered to any given patient must be determined empirically and will differ depending upon the condition of the patient. Relatively small amounts of the compounds can be administered at first, with steadily increasing dosages if no adverse effects ar noted. Of course, the maximum safe toxicity dosage as determined in routine animal toxicity tests should never be exceeded.

Optimally, the concentration of glucuronide conjugate to be administered may be sufficient to administer a concentration of thiol chelating compound from about 10 mg/kg body weight to about 2000 mg/kg body weight.

It is clear that any tumor cells having $\beta$-glucuronidase activity may be treatable in accordance with the present invention, with the remaining organs of the body being protected by the alkalinization step. Tumors which are known to have $\beta$-glucuronidase activity include solid breast tumors and their metastases, bronchogenic carcinoma and its metastases, and lymphomas.

It is also known that neoplasms which do not have high $\beta$-glucuronidase activity, and therefore cannot be treated in accordance with the present invention, include leukemias. It must be understood, however, that these lists are not meant to be complete, and that the prior art is aware of many other tumors that have $\beta$-glucuronidase activity. However, whether or not the art is presently aware that any given tumor has $\beta$-glucuronidase activity, this can be determined by any of the various methods of diagnosis discussed in the present specification. If it is determined that the tumor does indeed have $\beta$-glucuronidase activity, the therapeutic treatment of the present invention can be effectively used.

When it is desired to induce hyperthermia to increase $\beta$-glucuronidase activity, a method should be selected by which the temperature is raised as much as possible without risking damage to healthy portions of the body, such as the eyes. An increase of about 2° C. for whole body hyperthermia and as much as 4.5° C. for local hyperthermia is preferred. The hyperthermia should be timed to last about a hour at the time of greatest glucuronide concentration at the tumor site. For example, when local microwave treatment is selected, it should begin about one half hour after commencement of the intravenous conjugate drip and be continued for about one hour. The proper dosage of known pyrogens to achieve the desired degree of hyperthermia would be known to those skilled in the art, or could be easily empirically determined. A dosage of about 30 mg.day of dinitrophenol, for example, would be appropriate.

When estrogen or testosterone are to be administered, a dosage of 5-15 mg/body weight/day would provide the desired inducement of $\beta$-glucuronidase activity.

To treat patients suffering from cancers which exhibit $\beta$ glucuronidase activity, the dithiocarbamates are administered in the form of acetylated glucuronic acid conjugates or other forms of glucuronic acid conjugates, including the free acid conjugates or salts of the free acid or other esters of glucuronic acid conjugates. Capsules are formulated, generally containing approximately 0.6 gram/capsule of active ingredient. Generally, five capsules three times daily, providing nine grams/day of active ingredient are administered. The patient's serum is measured after a loading dosage is administered of the compound to maintain a level of approximately 1 mM of compound in the serum.

The conjugates of the present invention can be administered to patients suffering from $\beta$-glucuronidase-dependent cancers at doses ranging from about 1-15 grams/day of total dosage. Although it has been found that maintaining a serum level of about 1 mM of conjugate is desirable, serum levels ranging from about 0.1 mM to about 10 mM can be used, depending upon the patient's response to the treatment.

The conjugates of the present invention can be combined with a pharmaceutically acceptable carrier therefore, and optionally other therapeutic and/or prophylactic ingredients. The carriers must be "acceptable" in the sense of being compatible with the other ingredients of the formulation and not deleterious to the recipient thereof.

Pharmaceutical formulations suitable for oral administration wherein the carrier is a solid are most preferably presented as unit dose formulations such as boluses, capsules, and the like, as well as sachets or tablets each containing a predetermined amount of the active ingredient. A tablet may be made by compression or molding, optionally with one or more accessory ingredients. Compressed tablets may be prepared by compressing in a suitable machine the active conjugate in a free-flowing form, such as a powder or granules optionally mixed with a binder, lubricant, interdiluent, lubricating, surface active or dispersing agent. Molded tablets may be made by molding the active conjugate with an inert liquid diluent. Tablets may be optionally coated and, if uncoated, may optionally be scored. Capsules may be prepared by filling the active conjugate, either alone or in admixture with one or more accessory ingredients, into the capsule cases and then sealing them in the usual manner. Cachets are analogous to capsules wherein the active conjugate together with any optional accessory ingredient is sealed in a rice paper envelope.

Pharmaceutical formulations suitable for oral administration in which the carrier is a liquid may conveniently be presented as a solution in an aqueous liquid or a non-aqueous liquid, or an an oil-in-water or water-in-oil liquid emulsion.

Pharmaceutical formulations suitable for parenteral administration are conveniently presented in unit does or multidose container which are sealed after introduction of the formulation until required for use.

It should be understood that in addition to the aforementioned carrier ingredients the pharmaceutical formulations described above may include, as appropriate, one or more additional carrier ingredients such as diluents, buffers, flavoring agents, binders, surface active agents, thickeners, lubricants, preservative (including anti-oxidants) and the like, and substances included for the purpose of rendering the formulation isotonic with the blood of the intended recipient.

The pharmaceutical formulations may be any formulation in which the active compound may be administered and include those suitable for oral or parenteral (including intramuscular and intravenous) administration. The formulations may, where appropriate, be conveniently presented in discrete dosage units and may be prepared by any of the methods well known in the art of pharmacy. All of the methods include the step of bringing into association the active compound with liquid carriers or finely divided solid carriers of both and then, if necessary, shaping the product into the desired formulation.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A method for selectively treating tumor cells which have $\beta$-glucuronidase activity to inhibit the metabolism of said tumor cells comprising administering to a patient suffering from said tumor cells an effective amount of a conjugate made by conjugating glucuronic acid or a pharmaceutically acceptable ester or salt thereof to a thiol chelating compound of the formula:

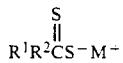

wherein $R^1$ and $R^2$ are selected from the group consisting of $C_1$-$C_6$ alkyl and $C_3$-$C_6$ cycloaliphatic groups, and M is selected from the group consisting of hydrogen, an electropositive, ionically bonded pharmaceutically acceptable metal, and the radical

wherein $R^3$ and $R^4$ are selected from the group consisting of $C_1$-$C_6$ alkyl and $C_3$-$C_6$ cycloaliphatic groups.

2. The method according to claim 1 wherein the conjugate is formed from the triacetylated form of glucuronic acid.

3. The method according to claim 2 wherein the conjugate is administered orally.

4. The method according to claim 1 wherein the thiol chelating compound is selected from the group consisting of diethyldithiocarbamate and pharmaceutically acceptable salts thereof.

5. The method according to claim 1 wherein, prior to administration of said conjugate, the patient is administered an alkalinizing agent in an amount sufficient to maintain the pH level of the non-tumor tissues of the patient at approximately 7.4 during the treatment with said conjugate.

6. The method according to claim 1 wherein, prior to administering said conjugate, the tumor cells are hyperacidified.

7. The method according to claim 1 further including the step of inducing hyperthermia at least at the site of the tumor being treated to an extent sufficient to increase substantially $\beta$-glucuronidase activity at the site without substantially affecting the overall health of the patient at the time of maximum conjugate concentration at the tumor.

8. The method according to claim 7 wherein said hyperthermia is induced locally at the tumor by administration of the glucuronide of a pyrogen, by microwave treatment or by passage of electrical current through the body.

9. The method according to claim 1 further including the step of administering estrogen or testosterone substantially simultaneously with administration of said conjugate, wherein the tumor is not estrogen- or testosterone-dependent.

10. A composition for selectively treating tumor cells which have $\beta$-glucuronidase activity comprising a pharmaceutically acceptable carrier and an effective amount of a conjugate made by conjugating a glucuronide compound selected from the group consisting of glucuronic acid and pharmaceutically acceptable esters and salts thereof to a thiol chelating compound of the formula:

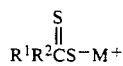

wherein $R^1$ and $R^2$ are selected from the group consisting of $C_1$-$C_6$ alkyl and $C_3$-$C_6$ cycloaliphatic groups, and M is selected from the group consisting of hydrogen, an electropositive, ionically bonded pharmaceutically acceptable metal, and the radical

wherein $R^3$ and $R^4$ are selected from the group consisting of $C_1$-$C_6$ alkyl and $C_3$-$C_6$ cycloaliphatic groups.

11. The composition according to claim 10 wherein the glucuronide compound is a triacetylated glucuronic acid.

12. The composition according to claim 11 wherein the glucuronide compound is methyl-(tri-O-acetyl-$\alpha$-D-glucopyranosyl)bromide uronate.

13. The composition according to claim 10 wherein the thiol chelating compound is selected from the group consisting of diethyldithiocarbamate and pharmaceutically acceptable salts thereof.

14. The composition according to claim 10 wherein the carrier is suitable for parenteral administration.

15. The composition according to claim 11 wherein the carrier is suitable for oral administration.

16. The method according to claim 1 wherein the tumor cells are selected from the group consisting of solid breast tumors, bronchogenic carcinoma, and lymphomas.

17. The method according to claim 16 wherein the tumor cells are solid breast tumors.

18. The method according to claim 1 wherein the conjugate is administered in sufficient amount to provide from about 19 mg/kg body weight to about 2000 mg/kg body weight of the thiol chelating compound.

* * * * *